United States Patent
Maksem et al.

(10) Patent No.: US 6,346,086 B1
(45) Date of Patent: Feb. 12, 2002

(54) ENDOCERVICAL AND EXOCERVICAL CELL COLLECTION DEVICE

(75) Inventors: John A. Maksem, Waukee, IA (US); Rodney W. Bosley, Jr., Bloomington; Kathren J. Sips, Spencer, both of IN (US)

(73) Assignee: Cook Urological Inc., Spencer, IN (US)

( * ) Notice: Subject to any disclaimer, the term of this patent is extended or adjusted under 35 U.S.C. 154(b) by 0 days.

(21) Appl. No.: 09/298,212

(22) Filed: Apr. 23, 1999

Related U.S. Application Data
(60) Provisional application No. 60/082,801, filed on Apr. 23, 1998.

(51) Int. Cl.[7] ............................................. A61B 10/00
(52) U.S. Cl. ........................ 600/569; 600/570; 600/572
(58) Field of Search ................................ 600/562, 569, 600/570, 572; 604/1, 2; 606/119

(56) References Cited

U.S. PATENT DOCUMENTS

| | | | |
|---|---|---|---|
| 2,701,559 A | | 2/1955 | Cooper ........................ 128/2 |
| 3,228,398 A | * | 1/1966 | Leonard et al. ............. 128/269 |
| 3,626,470 A | | 12/1971 | Antonides et al. .......... 128/2 R |
| 3,776,219 A | | 12/1973 | Brown ....................... 128/2 B |
| 3,877,464 A | * | 4/1975 | Vermes ....................... 600/572 |
| 3,881,464 A | | 5/1975 | Levene ....................... 128/2 B |
| 4,016,865 A | * | 4/1977 | Fredricks .................... 600/570 |
| 4,227,537 A | | 10/1980 | Suciu et al. ................ 128/756 |
| 4,235,244 A | | 11/1980 | Abele et al. ................ 128/749 |
| 4,448,205 A | * | 5/1984 | Stenkvist .................... 600/570 |
| 4,754,764 A | | 7/1988 | Bayne ........................ 128/756 |
| 4,759,376 A | | 7/1988 | Stormby .................... 128/756 |
| 4,763,670 A | | 8/1988 | Manzo ........................ 128/756 |
| 4,966,162 A | | 10/1990 | Wang ......................... 128/750 |

(List continued on next page.)

FOREIGN PATENT DOCUMENTS

| | | | |
|---|---|---|---|
| EP | 0363196 | 4/1990 | |
| GB | 2159420 | 12/1985 | |
| WO | 9116855 | 11/1991 | |
| WO | 93/01749 | * 2/1993 | ................. 600/570 |

Primary Examiner—Eric F. Winakur
Assistant Examiner—Charles Marmor, II
(74) Attorney, Agent, or Firm—James B. Hunt; Richard J. Godlewski (57) ABSTRACT

A medical device 10 for collecting both endocervical cells and exocervical cells from a human or veterinary patient includes an elongate handle 12 having first and second handle ends 14 and 16, an elongate foam portion 18 carried by one of the handle ends 14 or 16, and a disk-like foam portion 19 carried by either the same or the opposite handle end 14 or 16. The device 10 includes at least one base plate 30 or 32 connected to the handle 12, to which the elongate and disk-like foam portions 18 and 19 are affixed. The elongate foam portion 18 can be cylindrical in shape, while the disk-like portion 19 can be a convex disk 20 or a generally flat disk 60 or 80. The first foam portion 18 is positioned about a tip 40 or 48 carried by the first handle end 14, for example, connected to the first base plate 30. The first and second foam portions 18 and 19 can be carried on opposite ends 14 and 16 of the handle 12, or can be unitarily formed as a single foam portion 22 carried by the first handle end 14. The foam portions 18, 19, 20, 22, 60 and/or 80 comprise an open cell, reticulated foam (such as a polyester polyurethane foam of relatively large mean pore diameter, for example, 1 mm or larger) which is sufficiently pliant to take the shape of the internal and external surfaces of the cervix and is sufficiently abrasive to scrape an acceptably large number of cells from the internal and external surfaces of the cervix during use. In an alternative embodiment, the handle 12 includes a lumen 65 defined therein which is dimensioned to receive an endocervical brush 84 or other structure or object 82 therein, such as a guide wire, an endoscope, an optical fiber or a sensor. The device 10 can include the brush 84 or other object 82. The foam portion in that embodiment is preferably a perforate disk 80. The device 10 enjoys a superior combination of cell capture and relative patient comfort.

30 Claims, 5 Drawing Sheets

U.S. PATENT DOCUMENTS

| | | | |
|---|---|---|---|
| D317,361 S | 6/1991 | Stormby | D24/141 |
| 5,084,005 A * | 1/1992 | Kachigian | 600/569 |
| 5,133,361 A | 7/1992 | Cox et al. | 128/757 |
| 5,146,928 A | 9/1992 | Esser | 128/756 |
| 5,184,626 A | 2/1993 | Hicken | 128/756 |
| 5,201,323 A | 4/1993 | Vermuelen | 128/756 |
| 5,217,023 A | 6/1993 | Langdon | 128/756 |
| 5,253,652 A | 10/1993 | Fast | 128/756 |
| 5,370,128 A | 12/1994 | Wainwright | 128/756 |
| 5,623,941 A * | 4/1997 | Hedberg et al. | 600/572 |
| 5,713,369 A * | 2/1998 | Tao et al. | 600/569 |

* cited by examiner

ENDOCERVICAL AND EXOCERVICAL CELL COLLECTION DEVICE

CROSS-REFERENCE TO RELATED APPLICATIONS

This application claims priority of provisional application Ser. No. 60/082,801, filed Apr. 23, 1998.

TECHNICAL FIELD

This invention relates generally to medical devices, and more particularly to a device for collecting cells at least from around the outer opening of the cervix of a human or veterinary patient, and preferably for collecting both cells from the lining within the cervix and cells around the outer opening of the cervix of a human or veterinary patient.

BACKGROUND OF THE INVENTION

It has become virtually axiomatic that the best time to treat diseases such as cancer is when they are in their earliest phases. By necessity, the early treatment of cancer requires that it be detected early. A variety of known techniques for detecting cervical cancer entails the scraping or sampling of tissue from the uterine or endocervical canal, and from around the outer opening of the uterus (the cervical os). Tissues so obtained can be subjected to cytopathic or other examinations, perhaps the most common method of examination being the Pap (Papanicolaou) smear.

The known devices for exfoliating and collecting exocervical and endocervical tissue vary widely in complexity and utility. The most simple is a cotton swab introduced into the uterine canal. Wet spatulas have also been used to sample the exocervix and the uterine canal. Tissue samples have been aspirated through plastic or glass pipettes. Full dilation and curettage of the uterine canal has been employed, as have microcurettes. Brushes have been adapted to either exfoliate or collect endometrial tissue, but generally these have not been adapted to adequately perform both functions simultaneously. Generally, when the brush bristles are of a suitable length or stiff enough to exfoliate tissue well, they collect the exfoliated tissue poorly; and when the bristles are of a suitable length or flexible enough to collect tissue well, they fail to exfoliate sufficient tissue, or a sufficiently uniform sample of tissue.

One exception is the uterine endometrial tissue sample brush disclosed in U.S. Pat. No. 5,713,369 (Liang-Che Tao and John A. Maksem, Feb. 3, 1998). That brush, sold by COOK OB/GYN®, simultaneously performs both of these functions quite well, and includes a generally cylindrical arrangement of bristles. Another brush incorporating a generally cylindrical arrangement of bristles is sold by COOK OB/GYN® under the name DETECT® Cytology Brush. This brush includes a polystyrene handle which carries the bristles on it, and which is scored to permit a portion of the handle carrying the bristles to be snapped off and used in conjunction with popular STD (sexually transmitted disease) test kits. The use of each of these brushes is intentionally limited to endocervical sampling, however, and these brushes are not intended to additionally sample exocervical tissues.

A diagnostic device for obtaining cytological samples from both the exocervix and the endocervix is disclosed in U.S. Pat. No. 3,626,470 (H. J. Antonides et al., Dec. 7, 1971). The device of that patent comprises an elongated handle which carries on it a foamed or spongelike pledget molded on a platform member. The pledget is impregnated with a critical amount of a proteolytic enzyme which acts upon mucus encountered at or retrieved from sites of cellular sampling, thereby avoiding interference with the subsequent analysis of the collected materials. The pledget includes a nose portion surrounding a stem extending upwardly from the platform member. The pledget preferably comprises a silastic RTV (room temperature vulcanizing) foam, for example, a mixture of dimethyl polysiloxane fluid polymers and inert diatomaceous earth fillers. Silicone rubbers, polyurethanes and polyether urethanes and the like are also asserted to be useful. The pore size for a foamed silicone rubber ranges from 130 to 546 microns; more particularly, the mean and standard deviation are about 336.2 ±98.5 microns. The apparent specific gravity is in the range of from 0.177 to 0.292, and more particularly, a mean value and standard deviation of 0.223±0.028. Unfortunately, the disclosed variety of composition, pore size and specific gravity may not yield the best collection of cells, considering in combination the pliability of the foam (that is, the ability of the foam to take the shape of the internal and external surfaces of the cervix during sampling), the relative abrasiveness of the foam (increasing the number of cells which are scraped from the cervix) and whether the foam is open or closed cell (the former enhancing the retention and/or collection of the abraded cells).

U.S. Pat. No. 4,754,764 (I. D. Bayne, Jul. 5, 1988) similarly discloses a cervical cytology device which can include a disc for collecting exocervical cells, carried on a hollow shaft in which is telescopically received an endocervical brush for collecting cells. The disc and brush are preferably bristled, although urethane and polyurethane are suggested as materials for collecting cells. No specific physical arrangement of such other materials is disclosed, however.

The other conventional devices and techniques for sampling uterine endometrial tissue mentioned above have suffered their own drawbacks. Some sampling instrument diameters are uncomfortably large when inserted into the uterine canal, and their use can be sufficiently painful to the patient to require a general anesthetic. Some devices have undesirably low rates of successful insertion, while the use of others leads to unacceptably high rates of complications. Some devices have relatively poor yields (that is, inadequate sample sizes) when compared to conventional dilation and curettage. Full dilation and curettage, of course, entails its own trauma and disadvantages, including the infliction of open wounds requiring further post-procedural treatment. Many devices fail to obtain a large enough sample of tissue to ensure that localized abnormalities are detected.

It would be highly desirable to have a device which safely collects both exocervical and endocervical cells in relatively good patient comfort. It would also be highly desirable to have such a device which was simpler in construction than prior devices, and which did not include a relatively large plurality of individual bristles. It would further be desirable to have such a device in which the collecting portion or portions were sufficiently pliable to take on the shape of both the internal and external cervical surfaces being sampled. It would also be desirable to have such a device which was further adapted for use with other surgical devices, for example, for use with endoscopes, optic fibers, sensors, guide wires and other endocervical sample brushes.

SUMMARY OF THE INVENTION

The foregoing problems are solved and a technical advance is achieved in an illustrative medical device particularly adapted for abrading and collecting an acceptably large number of cells from at least the external surface of the cervix, and preferably from both the internal and external surfaces of the cervix. In one principal embodiment, the device of the present invention differs from prior devices for sampling cervical cells in that it employs a pair of foam portions each particularly suited for adequately sampling a different cervical surface.

More particularly, in this embodiment, the device of the present invention includes an elongate foam portion for sampling cells from the internal surface of the cervix, and a disk-like foam portion for sampling cells from the external surface of the cervix. The elongate foam portion and the disk-like foam portion can be carried on opposite ends of an elongate handle, or can be unitarily formed as a single foam portion carried by an end of the elongate handle. In either case, the elongate foam portion and the disk-like foam portion comprise an open cell, reticulated foam, preferably a foam as described in more detail below. The use of an open cell, reticulated foam permits the device of the present invention to enjoy superior sampling over prior cervical cell sampling devices, whether sampling only exocervical cells, or sampling both endocervical and exocervical cells.

In a second principal embodiment, the device of the present invention includes an open-celled, reticulate foam portion carried on the distal end of a hollow tube. The tube includes at least one lumen defined therein, which is dimensioned to receive one or more insertable structures or objects therein or therethrough. The insertable structure(s) or object(s) can be a guide wire, an endoscope, an optical fiber or a sensor. Preferably, the insertable structure or object is an endocervical brush having a plurality of bristles carried on an elongate brush handle. During introduction into a patient, the endocervical brush is preferably slidably received in the lumen of the hollow tube in a position such that the bristles of the endocervical brush are not exposed, but are instead contained within the tube lumen. Once the foam portion is adjacent the uterus, the endocervical brush is extended into the cervix, and rotated to obtain a sample of the endocervical cells.

In this embodiment, the device of the present invention can comprise not only the hollow tube and the open-celled, reticulate foam portion carried on it, but can further comprise the insertable structure(s) or object(s) with regard to which the lumen of the hollow tube is dimensioned.

Thus, in a first aspect, the present invention is directed to a medical device for collecting both endocervical cells and exocervical cells from a human or veterinary patient, comprising: an elongate handle having a first handle end and a second handle end opposite the first handle end; an elongate foam portion carried by one of the first handle end and the second handle end; and a disk-like foam portion carried by one of the first handle end and the second handle end; wherein the elongate foam portion and the disk-like foam portion comprise an open cell, reticulated foam and are sufficiently pliant to take the shape of the internal and external surfaces of the cervix when pressed by the handle against the internal and external surfaces of the cervix, respectively, and are sufficiently abrasive to scrape an acceptably large number of cells from the internal and external surfaces of the cervix when moved while being pressed by the handle against the internal and external surfaces of the cervix, respectively.

The elongate foam portion and the disk-like foam portion can be positioned on opposite ends of the handle, or can be unitarily formed as a single foam portion carried by one end of the handle, for example, the first handle end. Preferably, the elongate foam portion and the disk-like foam portion possess a relatively large mean pore diameter, on the order of or greater than about 1 mm. More preferably, the open cell, reticulated foam comprised by the elongate foam portion and the disk-like foam portion is a particular polyester polyurethane foam described in more detail below. The disk-like foam portion can be either a convex foam portion having a rounded or frustoconical surface opposite the handle, or a generally flat disk foam portion having a flat surface opposite the handle. The handle preferably includes at least one score permitting the handle to be separated manually at the at least one score. The at least one score is spaced from the elongate foam portion or the disk-like foam portion about 3 cm to about 5 cm.

The elongate foam portion preferably comprises a cylindrical body and a rounded end on the cylindrical body, and is about 0.6 cm in diameter. The disk-like foam portion is preferably about 1.9 cm to about 2.5 cm in diameter. Foam preferably extends about 1 mm beyond the handle end or tip on which the elongate foam portion and/or the disk-like foam portion is carried.

The handle can further comprise a tip carried by one of the first handle end and the second handle end, for example, the first handle end. The tip is of a size which is appropriate to assist dilation of the cervical os and then to provide subsequent support of the elongate foam portion during sampling, and can generally be about 7 French (2.3 mm) in diameter. The tip can include a bulbous head. At least the elongate foam portion is positioned about and is connected throughout its length to the tip. More preferably, the handle includes a hollow tube, and the device further comprises at least one base plate connected to one of the first handle end and the second handle end of the handle. At least one of the elongate foam portion and the disk-like foam portion is carried on the at least one base plate.

In a second aspect, the present invention is directed to a medical device for collecting both endocervical cells and exocervical cells from a human or veterinary patient, comprising: an elongate handle having a first handle end, a second handle end opposite the first handle end and a tip carried by the first handle end, the tip being generally about 7 French (2.3 mm) in diameter; a first base plate connected to the first handle end and a second base plate connected to the second handle end, the tip being carried on the first base plate; an elongate foam portion about 0.6 cm in diameter carried on the first base plate, comprising a cylindrical body and a rounded end on the cylindrical body, the elongate foam portion being positioned about and connected throughout its length to the tip; and a disk-like foam portion carried on the second base plate, the disk-like foam portion being about 1.9 cm to about 2.5 cm in diameter and including a rounded surface opposite the handle; wherein the elongate foam portion and the disk-like foam portion comprise an open cell, reticulated foam and are sufficiently pliant to take the shape of the internal and external surfaces of the cervix when pressed by the handle against the internal and external surfaces of the cervix, respectively, and are sufficiently abrasive to scrape an acceptably large number of cells from the internal and external surfaces of the cervix when moved while being pressed by the handle against the internal and external surfaces of the cervix, respectively; wherein the elongate foam portion and the disk-like foam portion possess a relatively large mean pore diameter; wherein the handle comprises a hollow tube having a first tube end to which the first base plate is connected, and a second tube end opposite the first tube end to which the second base plate is connected; and wherein the handle includes a pair of scores spaced one each about 3 cm to about 5 cm from the elongate foam portion and the second convex foam portion, the pair of scores permitting the handle to be separated manually at the pair of scores.

In a third aspect, the present invention is directed to a medical device for collecting both endocervical cells and exocervical cells from a human or veterinary patient, comprising: an elongate handle having a first handle end and a tip carried by the first handle end, the tip being generally about 7 French (2.3 mm) in diameter; a first base plate connected to the first handle end, the tip being carried on the first base plate; and a unitarily formed single foam portion carried by the first handle end on the first base plate, the single foam portion having an elongate foam portion about 0.60 cm in diameter and comprising a cylindrical body and a rounded end on the cylindrical body, and the single foam portion further having a disk-like foam portion positioned between the handle and the elongate foam portion, the disk-like foam portion being about 1.90 cm to about 2.00 cm in diameter and having a frustoconical surface opposite the handle; wherein the single foam portion is positioned about and connected throughout its length to the tip of the handle, comprises an open cell, reticulated foam and is sufficiently pliant to take the shape of the internal and external surfaces of the cervix when pressed by the handle against the internal and external surfaces of the cervix and is sufficiently abrasive to scrape an acceptably large number of cells from the internal and external surfaces of the cervix when moved while being pressed by the handle against the internal and external surfaces of the cervix, and possesses a relatively large mean pore diameter; wherein the handle comprises a hollow tube having a first tube end to which the first base plate is connected; and wherein the handle includes a score spaced about 3 cm to about 5 cm from the single foam portion which permits the handle to be separated manually at the score.

The foregoing aspects are all related to one principal embodiment of the present invention. Other aspects of the invention are related to another principal embodiment of the present invention. Accordingly, in another aspect, the present invention is directed to a medical device for collecting at least exocervical cells from a human or veterinary patient, comprising: an elongate handle comprising a hollow tube having a distal tip and a proximal end spaced from the distal tip, and at least one lumen defined therein, extending from the proximal end and to the distal tip; and at least one foam portion carried by the hollow tube and positioned about the distal tip of the hollow tube, the at least one foam portion comprising an open cell, reticulated foam which is sufficiently pliant to take the shape of at least the external surface of the cervix when pressed by the elongate handle against at least the external surface of the cervix, and which is sufficiently abrasive to scrape an acceptably large number of cells from at least the external surface of the cervix when moved while being pressed by the elongate handle against at least the external surface of the cervix; wherein the at least one lumen is dimensioned to receive at least one insertable structure or object therein or therethrough.

Preferably, the at least one insertable structure or object which the at least one lumen is dimensioned to receive comprises an endocervical brush, a guide wire, an endoscope, an optical fiber and/or a sensor. Also preferably, the device of the present invention additionally comprises the at least one insertable structure or object.

In a related aspect, the present invention is directed to a medical device for collecting at least exocervical cells from a human or veterinary patient, comprising: an elongate handle comprising a hollow tube having a distal tip, a proximal end spaced from the distal tip, at least one base plate connected to the distal tip and at least one lumen defined in the hollow tube, extending from the proximal end and to the distal tip; at least one foam portion carried on the at least one base plate of the hollow tube and positioned about the distal tip of the hollow tube, the at least one foam portion comprising an open cell, reticulated foam which is sufficiently pliant to take the shape of at least the external surface of the cervix when pressed by the elongate handle against at least the external surface of the cervix, and which is sufficiently abrasive to scrape an acceptably large number of cells from at least the external surface of the cervix when moved while being pressed by the elongate handle against at least the external surface of the cervix; and an endocervical brush; wherein the at least one lumen is dimensioned to receive the endocervical brush therein or therethrough; wherein the endocervical brush comprises a brush handle carrying a plurality of bristles thereon, and a round ball tip opposite the brush handle; wherein the at least one foam portion comprises a disk-like foam portion and an elongate foam portion unitarily formed with the disk-like foam portion, and possesses a relatively large mean pore diameter, the elongate foam portion being about 0.6 cm in diameter and the disk-like foam portion being about 1.9 cm to about 2.5 cm in diameter; and wherein the open cell, reticulated foam which is comprised by the at least one foam portion is a polyester polyurethane foam.

In a final aspect, the present invention is directed to a medical device for collecting at least exocervical cells from a human or veterinary patient, comprising: an elongate handle comprising a hollow tube having a distal tip, a proximal end spaced from the distal tip, at least one base plate connected to the distal tip and at least one lumen defined in the hollow tube, extending from the proximal end and to the distal tip; at least one disk-shaped foam portion carried on the at least one base plate of the hollow tube and positioned about the distal tip of the hollow tube, the at least one foam portion being about 1.9 cm to about 2.5 cm in diameter and comprising an open cell, reticulated foam which is sufficiently pliant to take the shape of at least the external surface of the cervix when pressed by the elongate handle against at least the external surface of the cervix, and which is sufficiently abrasive to scrape an acceptably large number of cells from at least the external surface of the cervix when moved while being pressed by the elongate handle against at least the external surface of the cervix; and an endocervical brush; wherein the at least one lumen is dimensioned to receive the endocervical brush therein or therethrough; wherein the endocervical brush comprises a brush handle carrying a plurality of bristles thereon, and a round ball tip opposite the brush handle; and wherein the open cell, reticulated foam which is comprised by the at least one disk-shaped foam portion is a polyester polyurethane foam.

The medical device of the present invention possesses significant advantages over prior devices for collecting endocervical and/or exocervical cells. Because its foam portions have good pliability, good relative abrasiveness and are open cell and reticulated, the device of the present invention safely collects both exocervical and endocervical cells in relatively good patient comfort. It is simpler in construction and therefore may be less expensive to manufacture than prior devices, since it does not include a relatively large plurality of individual bristles and therefore avoids the manufacturing step of connecting such individual bristles.

The medical device of the present invention also preferably includes an arrangement comprising one or more cellular structures each with at least one outermost layer of open and absorbent cells. In the arrangement, each cellular structure is supported by handle means and each structure is sufficiently contoured and pliant to adapt to the shape of the internal and/or external surfaces of a cervix to thereby collect endocervical cells and/or exocervical cells. As has been indicated, the cellular or foam structures on each end of the device arrangement can be on a single handle, multiple separate handles, or separate handles with separate collection means on a given end.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
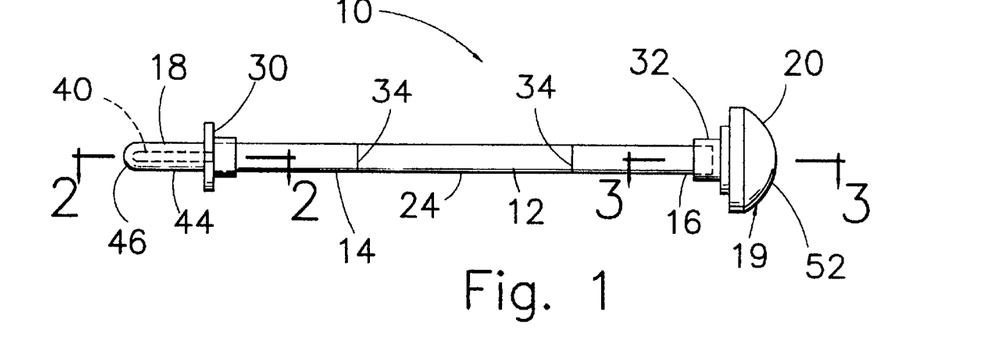
FIG. 1 is a side view of a first preferred embodiment of the present invention.
Figure 2:
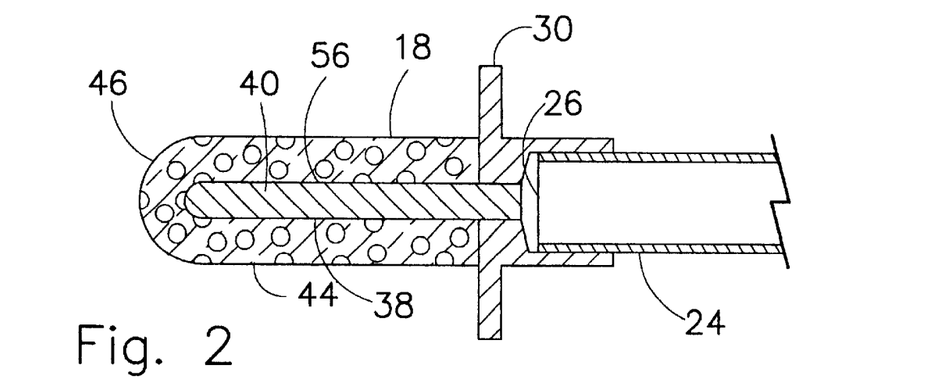
FIG. 2 is a cross-sectional view taken along line 2—2 of FIG. 1.
Figure 3:
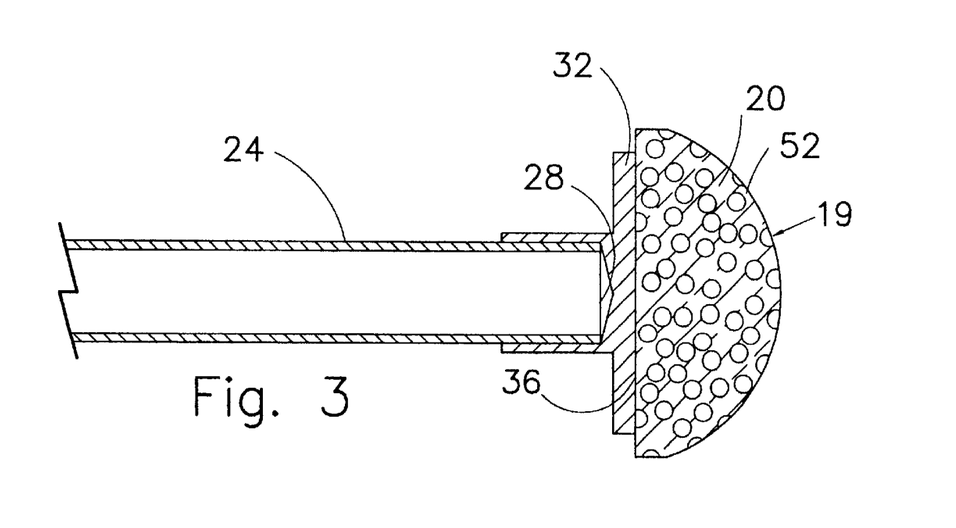
FIG. 3 is a cross-sectional view taken along line 3—3 of FIG. 1.

With reference first to FIGS. 1 to 3, a first embodiment of a medical device 10 according to the present invention for collecting both endocervical and exocervical cells from a human or veterinary patient is thereshown, in which the elongate foam portion and the disk-like foam portion mentioned above are separate and discrete from one another, and are carried by opposite ends of an elongate handle. This embodiment of the medical device 10 first comprises an elongate handle 12 having a first handle end 14 and a second handle end 16 opposite the first handle end 14. The device 10 also comprises an elongate foam portion 18 carried by one of the first handle end 14 and the second handle end 16, for example, as shown in FIGS. 1 and 2, by the first handle end 14. The medical device 10 further comprises a disk-like foam portion 19 also carried by one of the first handle end 14 and the second handle end 16, for example, as shown in FIGS. 1 and 3, by the second handle end 16. The disk-like portion 19 is preferably a convex foam portion 20 having an axially facing rounded surface 52 opposite the elongate handle 12. The elongate foam portion 18 and the disk-like foam portion 19 each comprise an open cell, reticulated foam.

Foam is an object commonly made up of closed bubbles or cells, and open cell foam is in effect a sponge-like object. It is to be understood that the outer surface at least of the foam of the type utilized in the present invention possesses open cells to increase adsorption and to achieve a sponge-like capability. One or more layers of the outer cells are considered open as indicated herein in order to achieve this sponge-like capability. This is indicated because such materials as polyester or polyurethane foam are commonly formed with closed cells, and this discussion is to clearly indicate that foam or sponge is to include at least one or more layers of the outer cells in an open condition or state to achieve the sponge-like capability for increasing adsorption. Although foam as indicated commonly includes closed cells, foam with either closed cells or open cells are commercially available. With open cell foams, the pore size or opening in the cells can be specified as is later indicated herein. Furthermore, it is contemplated that foam can include a combination of open and closed cells depending on the desired adsorption that is required.

With respect to the use of "convex" in the description herein, it is noted that all convex surfaces have curvature. However, it is to be contemplated that convex surfaces are not so restricted and that the frusto conical foam portion mentioned herein does have to be convex. It is also to be understood that all examples provided herein indicate "preferable" ranges or amounts and that other ranges or amounts are contemplated. These preferable ranges or amounts are not considered essential unless specifically indicated as such.

In use, the elongate handle 12 will be grasped by a healthcare practitioner or the patient so as to press the elongate foam portion 18 against the internal surface of the cervix and move the elongate handle 12 so as to scrape endocervical cells from the internal surface of the cervix and onto and into the elongate foam portion 18. (Access to the cervix will probably be most readily facilitated by use of a conventional speculum.) Similarly, the elongate handle 12 will be grasped to press the disk-like foam portion against the external surface of the cervix and move the elongate handle 12 so as to scrape exocervical cells from the external surface of the cervix and onto and into the disk-like foam portion 19. The collected cells on and in the elongate foam portion 18 and the disk-like foam portion 19 will then be analyzed in any appropriate manner. Both the elongate foam portion 18 and the disk-like foam portion 19 are sufficiently pliant to take the shape of the internal and external surfaces of the cervix when pressed by the elongate handle 12 against those surfaces, respectively, with good relative patient comfort. Moreover, both the elongate foam portion 18 and the disk-like foam portion 19 are sufficiently abrasive to scrape an acceptably large number of cells from the internal and external surfaces of the cervix, respectively, when moved against them while being pressed against them by the elongate handle 12. This combination of good relative patient comfort and adequate sampling is achieved by the use of an open cell, reticulated foam for the elongate foam portion 18 and the disk-like foam portion 19.

More particularly, the preferred open cell, reticulated foam used in the present invention is sufficiently rigid to ensure good abrasion and collection of cells, yet also possesses a relatively large mean pore diameter to ensure that good cell abrasion and collection are maintained while the foam remains pliant. Preferably, the elongate foam portion 18 and the disk-like foam portion 19 can possess a relatively large mean pore diameter, on the order of at least about 1 mm. This is a significantly larger mean pore diameter than is employed in the device of the Antonides et al. patent mentioned above, and along with the open cell, reticulated structure, provides the device 10 of the present invention with its superior properties. One preferred open cell, reticulated foam for use in the present invention is a polyester polyurethane foam having a nominal density of 1.9±0.1 lbs./ft.$^3$ (30.4±1.6 mg/cm$^3$, or a specific gravity of 0.0304±0.0016, less than 14% of the mean specific gravity of the foamed silicone rubber disclosed in the Antonides et al. patent). Such a foam can have a nominal cell count of about 28±5 pores per inch (11±2 pores per cm), a 25% compression force deflection (CFD) of about 0.50±0.10 lbs./in.$^2$ (3450±690 N/m$^2$), a minimum tensile strength of about 18 lbs./in.$^2$ (124,100 N/m$^2$), a 160% minimum elongation and a minimum tear strength of about 4.5 lbs. (0.80 kg/cm), and a maximum loss of 75% compression set at 50% deflection. Except for the nominal cell count, these numerical values are according to ASTM D 3574-86.

A more particularly preferred open cell, reticulated foam for use in the present invention has the same chemical composition, but has a smaller pore size, having a nominal cell count of about 30 pores per cm. Other open cell, reticulated foams of comparable rigidity, pliability and abrasiveness are also expected to be particularly useful in the practice of the present invention. It is believed that comparable suitable open cell, reticulated foams can be composed of urethanes, propylenes, ethylenes, polyimides, polyamides and silicones.

Figure 9:
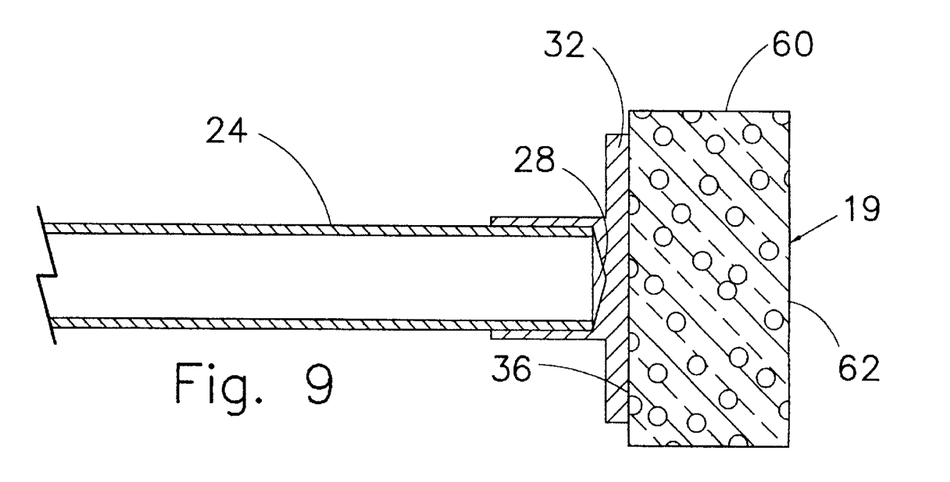
FIG. 9 is a cross-sectional view of still another preferred embodiment of the present invention.

A variety of shapes for the elongate foam portion 18 and the disk-like foam portion 19 are expected to be useful in the present invention. For example, the elongate foam portion 18 can be generally cylindrical in shape, comprising a cylindrical body 44 about 0.60 cm in diameter and a rounded end 46 on the cylindrical body 44. Also preferably, the disk-like foam portion 19, for example, the convex foam portion 20, is round in circumference and is about 1.90 cm to about 2.50 cm in diameter. The rounded surface 52 of the convex foam portion 20 can take the shape of a sphere, ellipsoid, paraboloid, oblate spheroid or any other convenient or appropriate shape. As shown in the alternative embodiment of FIGS. 4 and 5, described in more detail below, this surface can instead be frustoconical (that is, a truncated cone) in shape. Alternatively, as shown in the embodiment of FIG. 9, the surface of the disk-like foam portion 19 can simply be flat.

The elongate handle 12 can be formed in any convenient manner. For example, the elongate handle 12 can comprise a hollow tube 24 having a first tube end 26 and a second tube end 28. The elongate handle 12 can include at least one and preferably a pair of scores 34 on its surface, permitting the elongate handle 12 to be separated manually at the scores 34. This allows the elongate foam portion 18 and the disk-like foam portion 19 to be separated from the elongate handle 12 after cell collection, and placed in a suitable container for transport, shipping or delivery to the site at which the collected cells will be analyzed. For convenient use with conventional kits for analyzing samples for sexually transmitted diseases (STDs), each of the scores 34 can be spaced about 3 cm to about 5 cm from the closer of the elongate foam portion 18 and the disk-like foam portion 19.

The elongate foam portion 18 and the disk-like foam portion 19 are secured to the handle 12 in any convenient manner. For example, the device 10 of the present invention can comprise at least one base plate, more preferably a first base plate 30 and a second base plate 32, carrying on them the elongate foam portion 18 and the disk-like foam portion 19, which are thereby secured to the elongate handle 12. More particularly, the second base plate 32 is secured to the second tube end 28 in any suitable fashion, and the disk-like foam portion 19 affixed to the second base plate 32 by a layer 36 of a medical grade adhesive, thereby being carried by the second handle end 16. The second base plate 32 is preferably circular in circumference, and has a diameter somewhat smaller than the diameter of the disk-like foam portion 19, for example, about 0.625 in. (1.59 cm).

The first base plate 30 is similarly secured to the first tube end 26, but is drilled to receive therein a tip 40 about which the elongate foam portion 18 is positioned. The elongate foam portion 18 is affixed to the tip 40 and the first base plate 30 by a layer 38 of a medical grade adhesive, connecting the elongate foam member 18 to the tip 40 throughout the length of the elongate foam portion 18. Conveniently, the elongate foam portion 18 includes a longitudinal bore 56 which receives the tip 40 therein, and which is expanded when the tip 40 is received in the bore 56. The elongate foam portion 18 extends about 1 mm beyond the end of the tip 40.

Figure 6:
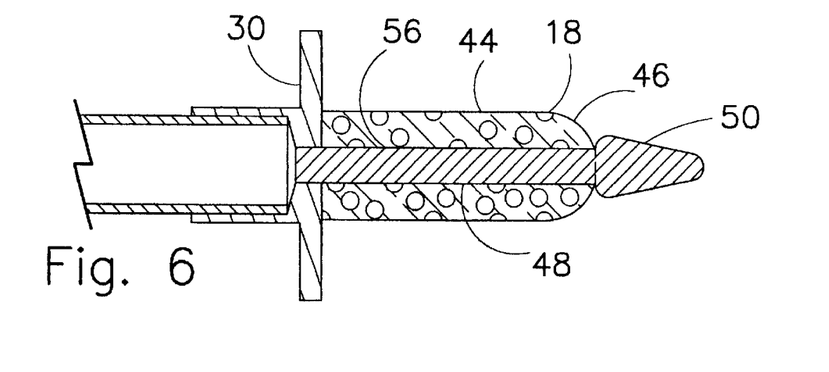
FIG. 6 is a cross-sectional view of a portion of another preferred embodiment of the present invention.

The tip 40 can be of any convenient shape and size which assists dilation of the cervical opening (the cervical os) and which supports the elongate foam portion 18 during sampling. For example, the tip 40 can be cylindrical in shape and about 7 French (2.3 mm, or about 0.09 in.) in diameter. However, the tip 40 can include structure which replaces or supplements the securement provided by the adhesive layer 38. An alternative tip 48 is shown in FIG. 6, still carried on the first base plate 30 and associated with the elongate foam portion 18, but having on it a bulbous or bullet-shaped head 50 which serves to retain the elongate foam portion 18 on it. The bulbous head 50 is wider than the diameter of the remainder of the tip 48, and can for example be about 0.118 in. (3.00 mm) in diameter.

Prior to positioning of the elongate foam portion 18 on either the tip 40 or the tip 48, the diameter of the bore 56 is smaller than the diameter of the tip 40 or 48, and preferably is significantly smaller than the diameter of the tip 40 or 48. For example, the initial diameter of the bore 56 can be about 0.050 in. (1.27 mm), in comparison to the 0.090 in. (2.3 mm) diameter of the tip 40, or of the tip 48 exclusive of the bulbous head 50.

Figure 4:
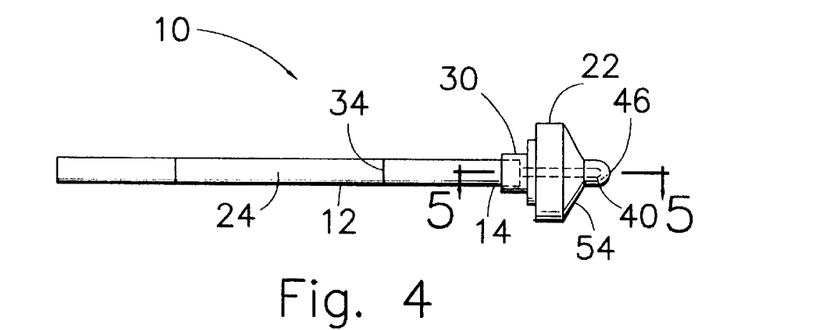
FIG. 4 is a side view of another preferred embodiment of the present invention.
Figure 5:
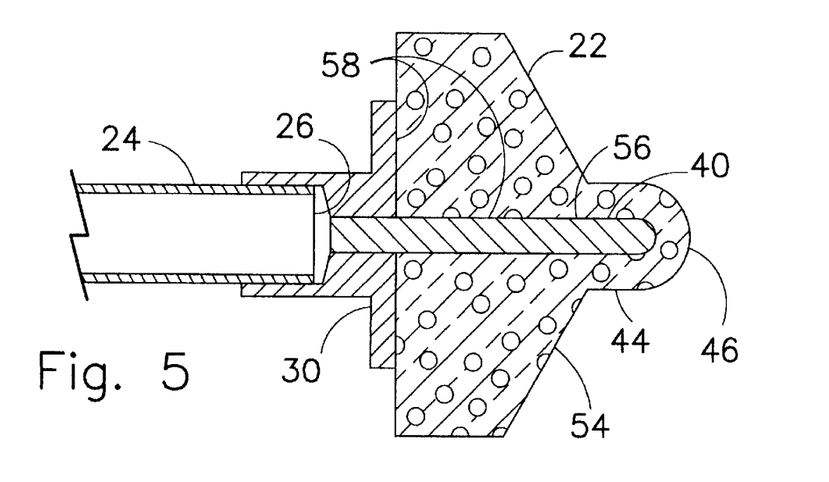
FIG. 5 is a cross-sectional view taken along line 5—5 of FIG. 4.

As indicated above, the elongate foam portion 18 and the disk-like foam portion 19 can be formed unitarily, rather than being carried on opposite ends of the handle 12. This may speed the performance of cell sampling under some circumstances. In the embodiment of the invention shown in FIGS. 4 and 5, the device 10 comprises a unitarily formed single foam portion 22 carried by the first handle end 14 of the elongate handle 12. The single foam portion 22 comprises the elongate foam portion 18 and the disk-like foam portion 19 (such as the convex foam portion 20 mentioned above), and can be composed of the same preferred open cell, reticulated foam described in detail above. The disk-like foam portion 22 of the single foam portion 22 can include the rounded surface 52 disclosed above. However, as shown in FIGS. 4 and 5, the single foam portion 22 can instead include a frustoconical surface 54 opposite the handle 12, which merges with the elongate foam portion 18. The single foam portion 22 is carried on the first base plate 30 and is affixed to it by a layer 58 of a medical grade adhesive. As in the first embodiment of the invention, the first base plate 30 is drilled to receive a tip 40 therein, about which the single foam portion 22 is positioned, with the elongate foam portion 18 of the single foam portion 22 secured to the tip 40 throughout the length of the elongate foam portion 18. The remaining elements of the embodiment shown in FIGS. 4 and 5 are the same as those of the embodiment shown in FIGS. 1 through 3. Most notably, a single score 34 is provided on the elongate handle 12 to permit manual separation of the elongate handle 12 at the score for the purpose mentioned above.

Both embodiments of the collecting device 10 of the present invention as described above include the hollow tube 24 of the elongate handle 12 and the pair of base plates 30 and 32 as separate elements connected to the opposite tube ends 26 and 28 of the tube 24. It is of course contemplated that these elements may instead be integrally molded or otherwise unitarily formed as a single piece constituting the elongate handle 12.

Figure 7:
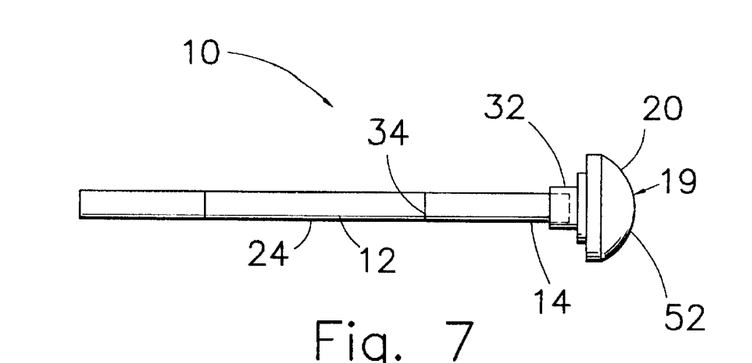
FIG. 7 is a side view of another preferred embodiment of the present invention.
Figure 8:
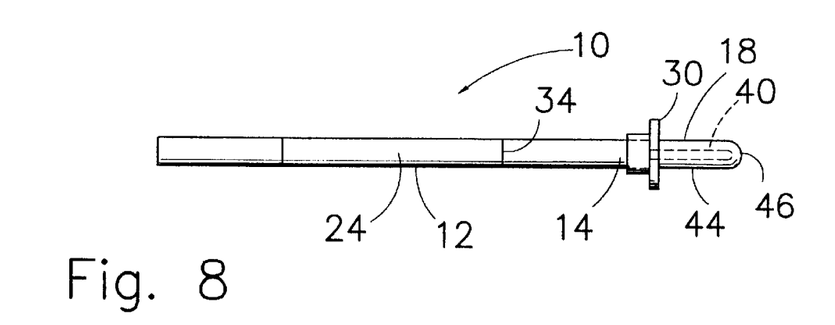
FIG. 8 is a side view of yet another preferred embodiment of the present invention.

A wide range of variations on the principles of the present invention should now become apparent. For example, the elongate foam portion 18 and the disk-like foam portion 19 need not be positioned on the same handle. Instead, as shown in FIGS. 7 and 8, each of the elongate foam portion 18 and the disk-like foam portion 19 can be carried on its own handle 12. The details of such an arrangement will be readily appreciated from the drawing; for brevity, the elements common to FIGS. 7 and 8, and the earlier Figures, will not be described a second time.

As another example, the disk-like foam portion 19 need not be convex in shape like the convex foam portion 20. Instead, the disk-like foam portion 19 can be configured as a generally flat disk-shaped foam portion 60 having an axially facing flat surface 62. The disk-shaped foam portion 60 can be incorporated in place of the convex foam portion 20 used in the embodiments shown either in FIGS. 1 and 3 or in FIG. 7. Conveniently, the details of attachment of the disk-shaped foam portion 60 to the hollow tube 24 of the handle 12 of the device 10 can be the same as those for attachment of the convex foam portion 20, and need not be repeated. A disk-shaped foam portion 60 having a diameter of about 0.945 in. (cm) and a thickness of about 0.350 in. (cm) may be particularly preferred.

It should also be apparent that the device 10 of the present invention can readily be modified for use in conjunction with a variety of other medical devices, such as endoscopes, optic fibers, sensors, guide wires, conventional bristle-type endocervical brushes, among others. The most direct way to modify the cell collection device 10 of the present invention is to provide the handle 12 of the device with one or more lumens or longitudinally extending throughbores to permit the introduction of such other medical devices into and/or through the device 10, or to permit the advancement of the device 10 along such other medical devices.

Figure 10:
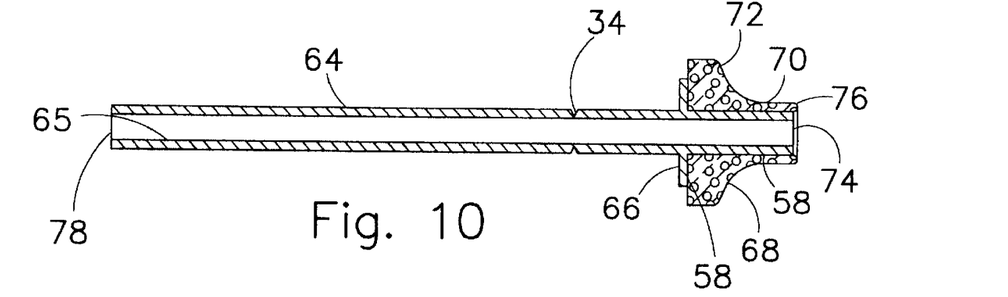
FIG. 10 is a cross-sectional view of another preferred embodiment of the present invention.

Accordingly, with reference now to FIG. 10, a second principal embodiment of the present invention is thereshown, in which the elongate handle 12 of the device 10 comprises a hollow tube 64. Unlike the hollow tube 24 described above, however, the interior of the tube 64 is not closed at either end. Instead, the tube 64 includes at least one lumen 65 defined therein, extending from the proximal end 78 of the tube to the distal tip 74 of the tube. The at least one lumen 65 is dimensioned to receive at least one insertable structure or object 82 therein or therethrough. (The insertable structure or object 82 is of course not shown in FIG. 10, but is present in FIGS. 11 and 12, exemplified by an endocervical brush 84.)

The device 10 as shown in FIG. 10 also comprises at least one foam portion carried by the hollow tube 64. For example, the foam portion can comprise a unitarily formed, perforate foam portion 68 having an elongated foam portion 70 and a convex foam portion 72. The unitarily formed foam portion 68 is comparable to the unitarily formed foam portion 22 described above and is positioned about the distal tip 74 of the hollow tube.

Like the unitarily formed foam portion 22, the unitarily formed foam portion 68 comprises an open cell, reticulated foam which is sufficiently pliant to take the shape of at least the external surface of the cervix when pressed by the elongate handle 12 against at least the external surface of the cervix, and which is sufficiently abrasive to scrape an acceptably large number of cells from at least the external surface of the cervix when moved while being pressed by the elongate handle 12 against at least the external surface of the cervix. Unlike the elongate foam portion 18 of the unitarily formed foam portion 22, however, the distal tip 76 of the elongated foam portion 70 (and thus of the unitarily formed foam portion 68) is open, extending about 1 mm beyond the distal tip 74 of the hollow tube 64. This allows access to the lumen 65 formed in the tube 64, and in particular, allows the at least one insertable structure or object 82 to be received in or through the lumen 65.

Conveniently, the unitarily formed foam portion 68 is affixed by a medical grade adhesive 58 to a base plate unitary or integral with the hollow tube 64. The hollow tube 64 includes a circumferential score 34 permitting the tube 64 to be split manually at a location spaced from the base plate 66. Such splitting may facilitate engagement or removal of an endoscope or other structure or object 82 from the lumen 65. Of course, more than one lumen 65 may be formed in the hollow tube 64; for clarity of presentation, however, such additional lumens are not shown in the Figures. Different structures or objects 82 can be positioned in the different lumens, if present, and the proximal end 78 of the hollow tube 64 may be closed or sealed temporarily, by means not shown, when required in the particular sampling procedure being performed.

Figure 11:
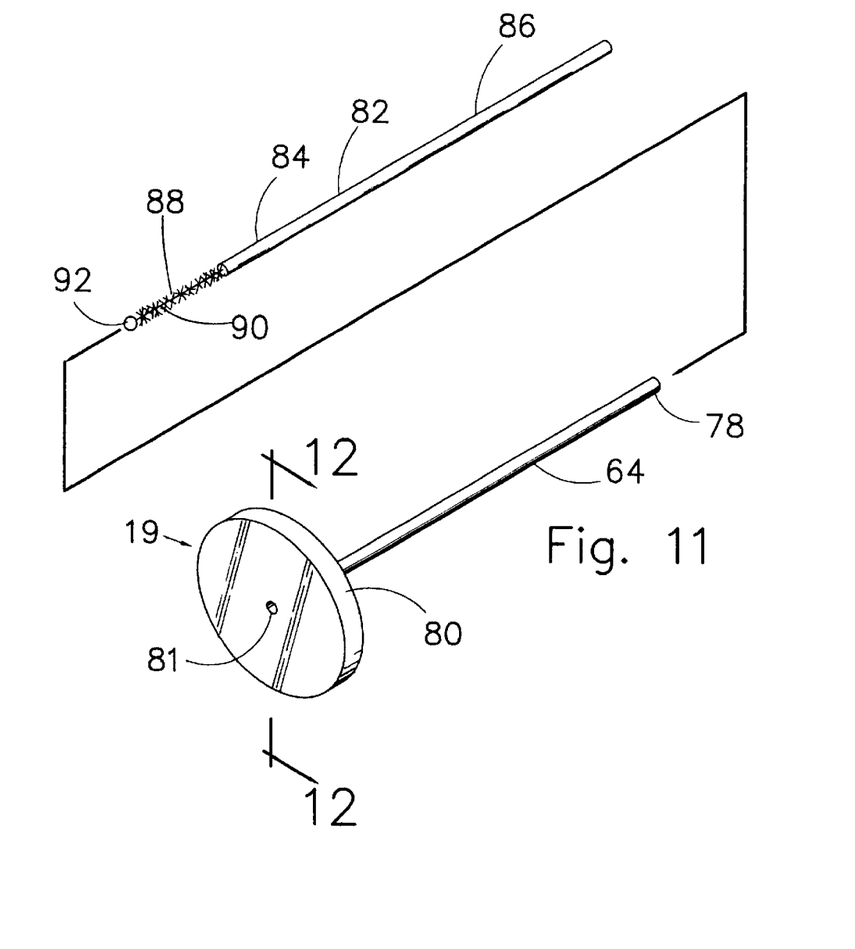
FIG. 11 is a perspective view of yet another preferred embodiment of the present invention.
Figure 12:
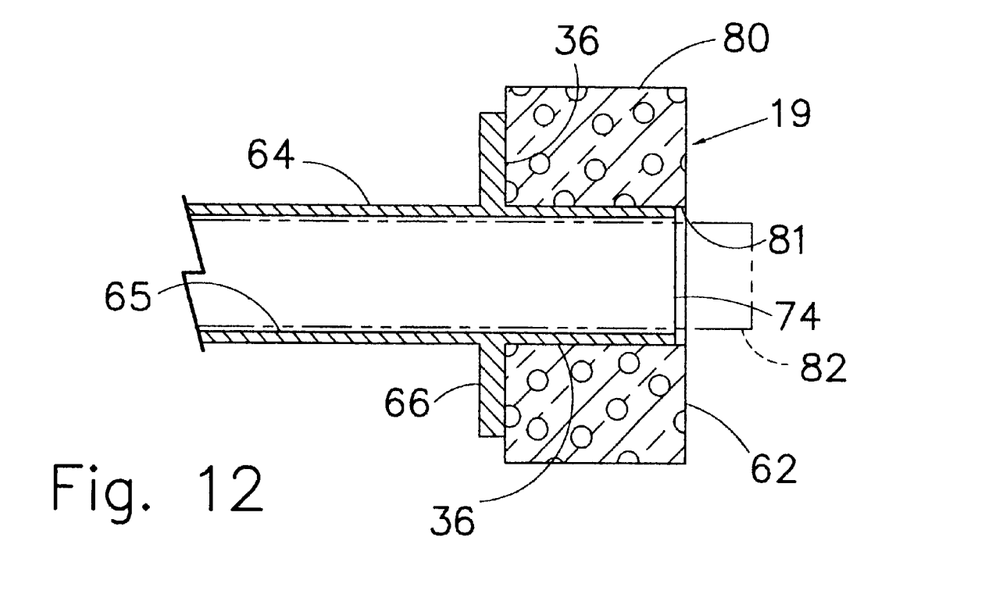
FIG. 12 is a cross-sectional view taken along line 12—12 of FIG. 11.

With reference now to FIGS. 11 and 12, a further modification of this embodiment of the present invention is thereshown in which the disk-like foam portion 19 is configured as a generally flat disk-shaped foam portion 80 having a distal opening 81 therein. The distal opening 81 allows an insertable structure or object 82, such as a conventional endocervical sample brush 84, to be insertably received in the lumen 65 through either the proximal end 78 of the hollow tube 64 or the distal tip 76 of the tube 64. How and when the endocervical brush 84 is received in, extended from or removed from the lumen 65 will depend upon the specific sampling procedure being performed.

The endocervical brush 84 preferably comprises an elongate brush handle 86 carrying a plurality of bristles 88 thereon. The bristles 88 are connected to one another and to the brush handle 86 by a twisted wire 90. The brush 84 preferably includes a round ball tip 92 connected to the twisted wire 90 opposite the brush handle 86. The round ball tip 92 improves passage of the brush 84 and bristles 88 into and through the cervix, and helps prevent the distal end of the brush 84 from getting caught in the cervical crypts. The brush 84 may of course include the preferred open cell, reticulated foam as a cell collecting medium, instead of the bristles 88.

The compositions, sizes and proportions of the various foam portions shown in FIGS. 10 to 12 are preferably the same as those for the foam portions shown in the prior Figures. Moreover, as indicated above, the device 10 of the present invention not only comprises the single or plurallumen hollow tube 64 and the associated foam portions described above, but can further comprise the endocervical brush 84 or other insertable structure(s) or object(s) 82 receivable in the lumen(s) 65 formed in the tube 64.

It should be clear that the present invention thus provides a cervical cell collecting device 10 which possesses significant advantages over prior devices for that purpose. Because its open cell, reticulated foam portions have good pliability and good relative abrasiveness, the device of the present invention safely collects adequately large numbers of both exocervical and endocervical cells in relatively good patient comfort. Moreover, the device 10 of the present invention is simpler in construction than prior devices and therefore may be less expensive to manufacture, since it does not include a relatively large plurality of individual bristles and therefore avoids the manufacturing step of connecting such individual bristles.

The details of the construction or composition of the various elements of the medical device 10 of the present invention not otherwise disclosed are not believed to be critical to the achievement of the advantages of the present invention, so long as the elements possess the strength or flexibility needed for them to perform as disclosed. The selection of any such details of construction are believed to be well within the ability of one of even rudimentary skills in this area, in view of the present disclosure.

INDUSTRIAL APPLICABILITY

The present invention is useful for collecting cells from the endocervix and the exocervix, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A medical device for collecting both endocervical cells and exocervical cells from a human or veterinary patient, comprising:

an elongate handle having a first handle end and a second handle end opposite the first handle end;

an elongate foam portion carried by one of the first handle end and the second handle end; and a disk-like foam portion carried by one of the first handle end and the second handle end;

wherein the elongate foam portion and the disk-like foam portion comprise an open cell, reticulated foam having a relatively large mean pore diameter on the order of at least about 1 mm, and are sufficiently pliant to take the shape of the internal and external surfaces of the cervix when pressed by the elongate handle against the internal and external surfaces of the cervix, respectively, and are sufficiently abrasive to scrape an acceptably large number of cells from the internal and external surfaces of the cervix when moved while being pressed by the elongate handle against the internal and external surfaces of the cervix, respectively.

2. The device according to claim 1, wherein one of the elongate foam portion and the disk-like foam portion is carried by the first handle end, and wherein the other of the disk-like foam portion and the elongate foam portion is carried by the second handle end.

3. The device according to claim 1, wherein the elongate foam portion and the disk-like foam portion are unitarily formed as a single foam portion carried by the first handle end.

4. The device according to claim 1, wherein the disk-like foam portion is a convex foam portion having a rounded surface opposite the elongate handle.

5. The device according to claim 1, wherein the disk-like foam portion is a flat disk foam portion having a flat surface opposite the elongate handle.

6. The device according to claim 1, wherein the elongate handle includes at least one score permitting the elongate handle to be separated manually at the at least one score.

7. The device according to claim 1, wherein the elongate handle further comprises a tip carried by one of the first handle end and the second handle end, and wherein at least the elongate foam portion is positioned about the tip.

8. The device according to claim 1, comprising at least one base plate connected to one of the first handle end and the second handle end of the elongate handle, and wherein at least one of the elongate foam portion and the disk-like foam portion is carried on the at least one base plate.

9. The device according to claim 1, wherein the elongate handle comprises a hollow tube.

10. The device according to claim 9, wherein the hollow tube has a distal tip spaced from the distal tip, and includes at least one lumen defined therein, extending from the proximal end and to the distal tip.

11. The device according to claim 10, wherein at least the disk-like foam portion is perforate.

12. The device according to claim 11, wherein the disk-like foam portion is a flat disk foam portion having a flat surface opposite the elongate handle.

13. The device according to claim 11, wherein the open cell, reticulated foam which is comprised by the elongate foam portion and the disk-like foam portion is a polyester polyurethane foam.

14. The device according to claim 1, comprising a base plate connected to the first handle end carrying the elongate foam portion thereon, and a base plate connected to the second handle end carrying the disk-like foam portion.

15. The device according to claim 14, wherein a tip of the handle extends beyond the base plate connected to the first handle end, and the elongate foam portion is positioned about the tip.

16. A medical device for collecting at least exocervical cells from a human or veterinary patient, comprising:

an elongate handle comprising a hollow tube having a distal tip and a proximal end spaced from the distal tip, and at least one lumen defined therein, extending from the proximal end and to the distal tip; and at least one foam portion carried by the hollow tube and positioned about the distal tip of the hollow tube, the at least one foam portion comprising an open cell, reticulated foam having a relatively large mean pore diameter, on the order of at least about 1 mm, which is sufficiently pliant to take the shape of at least the external surface of the cervix when pressed by the elongate handle against at least the external surface of the cervix, and which is sufficiently abrasive to scrape an acceptably large number of cells from at least the external surface of the cervix when moved while being pressed by the elongate handle against at least the external surface of the cervix;

wherein the at least one lumen is dimensioned to receive at least one insertable structure or object therein or therethrough.

17. The device according to claim 16, wherein the lumen is dimensioned to receive therein an insertable structure or object which comprises at least one of an endocervical brush, a guide wire, an endoscope, an optical fiber and a sensor.

18. The device according to claim 17, further comprising at least one of an endocervical brush, a guide wire, an endoscope, an optical fiber and a sensor.

19. The device according to claim 16, wherein the at least one foam portion comprises a disk-like foam portion.

20. The device according to claim 19, wherein the disk-like foam portion is a convex foam portion having a rounded surface opposite the elongate handle.

21. The device according to claim 19, wherein the disk-like foam portion is a flat disk foam portion having a flat surface opposite the elongate handle.

22. The device according to claim 16, wherein the at least one foam portion comprises a disk-like foam portion and an elongate foam portion.

23. The device according to claim 22, wherein the disk-like foam portion and the elongate foam portion are unitarily formed as a single foam portion carried by the distal tip of the hollow tube.

24. The device according to claim 16, wherein the elongate handle includes at least one score permitting the elongate handle to be separated manually at the at least one score.

25. The device according to claim 16, further comprising at least one base plate connected to the distal tip of the hollow tube, wherein the at least one foam portion is carried on the at least one base plate.

26. The device according to claim 16, wherein the open cell, reticulated foam which is comprised by the at least one foam portion is a polyester polyurethane foam.

27. The device according to claim 16, comprising a base plate connected to a first handle end of the elongate handle carrying an elongate foam portion thereon, and a base plate connected to a second handle end of the elongate handle opposite the first handle end carrying the disk-like foam portion.

28. The device according to claim 27, wherein a tip of the handle extends beyond the base plate connected to the first handle end, and the elongate foam portion is positioned about the tip.

29. A medical device for collecting at least exocervical cells from a human or veterinary patient, comprising:

an elongate handle comprising a hollow tube having a distal tip, a proximal end spaced from the distal tip, at least one base plate connected to the distal tip and at least one lumen defined in the hollow tube, extending from the proximal end and to the distal tip;

at least one disk-shaped foam portion carried on the at least one base plate of the hollow tube and positioned about the distal tip of the hollow tube, the at least one foam portion being about 1.9 cm to about 2.5 cm in diameter and comprising an open cell, reticulated foam having a relatively large mean pore diameter, on the order of at least about 1 mm, which is sufficiently pliant to take the shape of at least the external surface of the cervix when pressed by the elongate handle against at least the external surface of the cervix, and which is sufficiently abrasive to scrape an acceptably large number of cells from at least the external surface of the cervix when moved while being pressed by the elongate handle against at least the external surface of the cervix; and an endocervical brush;

wherein the at least one lumen is dimensioned to receive the endocervical brush therein or therethrough;

wherein the endocervical brush comprises a brush handle carrying a plurality of bristles thereon, and a round ball tip opposite the brush handle; and wherein the open cell, reticulated foam which is comprised by the at least one disk-shaped foam portion is a polyester polyurethane foam.

30. An arrangement comprising one or more cellular structures each with at least one outermost layer of open and absorbent cells, wherein the or each cellular structure is supported by a portion of a handle, and wherein the or each structure is sufficiently contoured and pliant to adapt to the shape of the internal or external surfaces of a cervix, or both, to thereby collect endocervical cells or exocervical cells or both.

* * * * *